United States Patent [19]

Kawaguchi et al.

[11] Patent Number: 4,868,162
[45] Date of Patent: Sep. 19, 1989

[54] ANTIVIRAL AGENT

[75] Inventors: Takeo Kawaguchi, Tokyo; Shigeki Fujinaga; Yoshiki Suzuki, both of Hino, all of Japan

[73] Assignee: Teijin Limited, Osaka, Japan

[21] Appl. No.: 28,841

[22] PCT Filed: Jul. 21, 1986

[86] PCT No.: PCT/JP86/00383

§ 371 Date: Mar. 23, 1987

§ 102(e) Date: Mar. 23, 1987

[87] PCT Pub. No.: WO87/00435

PCT Pub. Date: Jan. 29, 1987

[30] Foreign Application Priority Data

Jul. 22, 1985 [JP] Japan .................. 60-160115

[51] Int. Cl.$^4$ .......................................... A61K 31/70
[52] U.S. Cl. ........................................ 514/50; 514/934
[58] Field of Search ............. 536/23; 514/50, 934

[56] References Cited

U.S. PATENT DOCUMENTS 3,323,994  6/1967  Grötsch ..................... 514/50
3,352,849  11/1987  Shen et al. ................. 536/23

FOREIGN PATENT DOCUMENTS 2807588  8/1979  Fed. Rep. of Germany ........ 514/50
4157     6/1966  France .
1080491  8/1967  United Kingdom .

OTHER PUBLICATIONS

Kanzawa et al., the Chemical Abstracts, 95:197203j (1981).
Kawaguchi et al., the Chemical Abstracts, 103:31965t (1985).
Supplementary European Search Report.

Primary Examiner—John W. Rollins
Attorney, Agent, or Firm—Sughrue, Mion, Zinn, Macpeak & Seas

[57] ABSTRACT

A method of inhibiting viral replication in a cell comprising administering an effective amount of an esterified derivative of 5-halogenated-2'-deoxy-uridine expressed by the following formula (I)

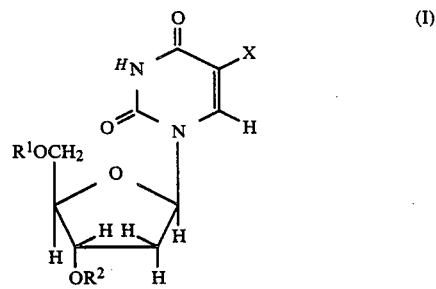

wherein X represents any one of F, Cl, and Br; $R^1$ and $R^2$ may be identical or different from each other, each representing an aliphatic acyl group comprising two or more carbon atoms or an aromatic acyl group comprising 7 or more carbon atoms.

2 Claims, No Drawings

ANTIVIRAL AGENT

TECHNICAL FIELD

This invention relates to an antiviral agent. More particularly this invention relates to an antiviral agent which displays a high level of antiviral effect with small doses and yet its toxicity to normal cells is low.

BACKGROUND ART

The replication of a viral DNA in a viral infected cell is conducted independently of the DNA replication cycle of the host cell, and it proceeds at much higher level in both speed and volume as compared with the replication of DNA which takes place in a normal cell. In view of this fact, reports have been made and published on several kinds of compounds which inhibit the DNA formation of a virus based on the difference in the process of DNA replication between a normal cell and a virus infected cell such as (E)-5-(2-bromovinyl)-2'-deoxyuridine [Nucleic Acid Research, 10, 6051 (1982), European Patent Publication No. 61283], 2'-nor-2'-deoxyguanosine [Biochemical and Biophysical Research Communications, 116, 360 (1983)], 9-(2-hydroxy-3-nonyl) adenine [Biochemical Pharmacology, 32, 3541 (1983)], 9-(2-hydroxyethoxymethyl)guanine [Chemotherapy, 25, 279 (1979), Journal of Biological Chemistry, 253, 8721 (1978)], 9-β-D-Arabinofuranosyladenine [British Medical Journal, 2, 531 (1978)], etc.

Besides the aforementioned ones, it is reported that 5-halogenated pyrimidinenucleoside strongly inhibits the DNA formation in a virus infected and normal eucaryotic cell [Biochemical and Biophysical Research Communications, 86, 112 (1979), Pharmacology Review, 29, 249 (1977), Biochemica et Biophysica Acta, 518, 31 (1978), Proceedings of the Society for Experimental Biology and Medicine, 154, 439 (1977), Cancer Research, 36, 4480 (1976)]. However, 5-halogenated pyrimidinenucleoside in its original condition is too strong in its function to inhibit the DNA formation in an animal cell and 5-iodo-2'-deoxyuridine has a limited use as an antiviral agent only for herpetic keratitis. Also, 5-fluoro-2'-deoxyuridine is efficacious as an antitumor drug [Cancer Research, 38, 3784 (1978)], and it is also reported that its ester derivatives have an antitumor activity [Cancer Chemotherapy and Pharmacology, 6, 19 (1981), Chemical and Pharmaceutical Bulletin, 33, 1652 (1985)]; however, nothing has yet been made known about its antiviral activity.

DISCLOSURE OF THE INVENTION

As the result of an intensive research conducted on masked type compounds obtained by modifying the hydroxyl group of 5-halogenated-2'-deoxyuridine with various substituents with the purpose of obtaining a drug of low toxicity for normal animal cell while inhibiting the proliferation of virus even when taken in small dosage by inducing a compound, which is inhibitive of the DNA formation, into derivatives, the present inventors have come to find that various compounds obtained by esterifying the hydroxyl group of 5-halogenated-2'-deoxyuridine with an aliphatic or aromatic acyl group not only display the effect of inhibiting the proliferation of virus at high level when taken in very small dosage but also show a high therapeutic index while having a low toxicity against normal cells, thus completing the present invention.

The present invention relates to an antiviral agent characterized by containing as an active ingredient an esterified derivative of 5-halogenated-2'-deoxyuridine expressed by the following formula (I)

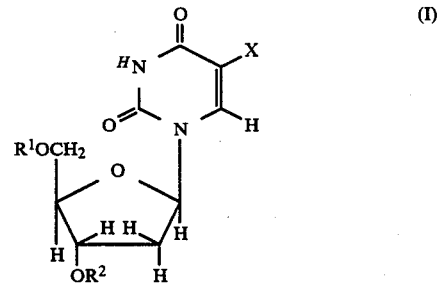

wherein X represents any one of F, Cl and Br; $R^1$ and $R^2$ may be identical or different from each other, each representing an aliphatic acyl group comprising two or more carbon atoms, or an aromatic acyl group comprising seven or more carbon atoms.

BEST MODE OF CARRYING OUT THE INVENTION

In the formula (I) of this invention, X represents F, Cl or Br, of which F and Cl are preferable.

$R^1$ and $R^2$ are identical or different from each other, each representing a hydrogen atom, or an aliphatic acyl group comprising two or more carbon atoms, or an aromatic acyl group comprising six or more carbon atoms.

As the aliphatic acyl group of this type, acetyl, butyryl, hexanoyl, octanoyl, decanoyl, dodecanoyl, tetradecanoyl, and hexadecanoyl, for instance, may be mentioned, and as the aromatic acyl group, there are benzoyl, toluoyl, and naphthoyl.

As the concrete examples of this invention, there are, for instance, 3',5'-dioctanoyl-5-fluoro-2'-deoxyuridine, 3',5'-didodecanoyl-5-bromo-2'-deoxyuridine, 3'5'-ditetradecanoyl-5-fluoro-2'-deoxyuridine, 3',5'-dihexanoyl-5-fluoro- 2'-deoxyuridine, 3',5'-didecanoyl-5-fluoro-2'-deoxyuridine, 3',5'-didodecanoyl-5-fluoro-2'-deoxyuridine, 3',5'-dihexadecanoyl-5-fluoro-2'-deoxyuridine, 5',5'-dibenzoyl-5-fluoro-2'-deoxyuridine, and 3',5'-ditoluoyl-5-fluoro-2'-deoxyuridine.

The compounds of this invention can all be synthesized according to any known method such as the one shown in the Biochemical Pharmacology, 14, 1605 (1965). For example, their synthesis can be achieved according to an ordinary method in which 5-halogenated-2'-deoxyuridine is allowed to react with a corresponding acid halide or acid anhydride in the presence of such an organic base as pyridine and trialkylamine.

When the compound expressed by formula (I) according to this invention has its antiviral effect examined by observing its activity of decreasing the number of plaque forming cells with the use of Vero cells (cell system obtained by inoculating the strain African green monkey's kidney cells with the herpes simplex type I), the result shows that it displays a strong inhibitory effect against the proliferation of virus when it is taken in a very small dose equivalant to 1/15 to 1/400 of 9-(2-hydroxyethoxymethyl) guanine (Acyclovir) and that the minimum toxic dose to cells is as high as 1,500 to 10,000 times the density at which it displays the inhibitory effect against the proliferation of virus. When compared with 5-fluoro-2'-deoxyuridine, which is an underived form of 5-halogenated-2'-deoxyuridine, the compound of formula (I) has the minimum toxic dose against cells as high as 1,000 times and shows an excellent therapeutic index while its antiviral effect is at the same level.

For instance, 3',5'-dioctanoyl-5-fluoro-2'-deoxyuridine of this invention shows the effective dose (EDs), which is required of the compound for reducing the number of plaques formed on virus by 50% experimented with the use of a cell strain obtained by inoculating the Vero cells with 10,000 pfu/ml of herpes simplex type I (KOS strain), as low as about 1/400 (0.018 μg/ml) of Acyclovia for obtaining the same effect. The therapeutic index, which is indicated by the value of a ratio of the minimum toxic dose (MTD), which shows the toxicity to normal cells, to EDs, is 5,600, being remarkably high as compared with 140 of Acyclovir.

The ester derivatives of 5-halogenated-2'-deoxyuridine of this invention are administered orally or parenterally such as subcutaneously, intramuscularly, intravenously, intra-arterially, percutaneously, intrarectally, as eye drops, intravaginally, intrauterinely, and intracerebrally.

As the dosage form for oral administration, a tablet, pill, granule, powder, liquid preparation, suspension, and capsule, for instance, may be mentioned.

Tablets are prepared according to an ordinary method with the use of such excipients as lactose, starch, crystalline cellulose, and hydroxypropyl cellulose; such binders as carboxymethyl cellulose, methyl cellulose, polyvinylpyrrolidone, and sodium alginate; and such disintegrators as calcium carboxymethyl cellulose and starch. Pills, powder, and granules can also be prepared according to an ordinary method with the use of the aforementioned excipients, etc. Liquid preparations and suspensions are prepared according to an ordinary method with the use of such glycerol-esters as tricaprylin, triacetin, and trilaurin; such vegetable oils as coconuts oil and fractionated coconuts oil and such alcohols as ethanol. Capsules are prepared by filling hard gelatin capsules with granules or powder, or by filling soft elastic gelatin capsules with a liquid preparation.

As the dosage form for the subcutaneous, intramuscular, intracerebral, intravenous, and intra-arterial administration use, there is a parenteral injection in the form of an aqueous or nonaqueous liquid preparation or suspension. In preparing a nonaqueous liquid preparation or suspension, propylene glycol, polyethylene glycol, olive oil, and ethyl oleate are used and an antiseptic and stabilizer are added thereto, if necessary. An injection is usually sterilized by filtration by means of bacterial filter method or by addition of an antimicrobial as case may require.

As the dosage form for percutaneous administration, ointments and creams, for instance, may be mentioned. Ointments are manufactured according to an ordinary method with the use of such fatty oils as castor oil and olive oil, and vaseline. Creams are manufactured according to an ordinary method with the use of fatty acid and such emulsifying agents as diethylene glycol and sorbitan monofatty acid ester.

Soft elastic gelatin capsules or suppositories prepared with the use of cacao butter are used for intrarectal, intravaginal, and intrauteral administration.

As the dosage form for application to eyes, eye drops and emulsion eye drops prepared with the use of a boric acid solution, or eye ointments prepared with the use of vaseline or liquid paraffin may be mentioned.

The dose of the ester derivative of 5-halogenated-2'-deoxy uridine of this invention varies depending upon the age, sex, condition of a patient, and dosage form; however, it is usually in the range of 0.002 to 2.0 mg/kg/day, preferably 0.01 to 1.0 mg/kg/day.

The amount of the ester derivative of 5-halogenated-2'-deoxyuridine to be contained in the pharmaceutical preparations of this invention is determined based on the aforementioned dose. For example, a capsule, injection, and suppository are ordinarily made to contain 0.1 to 100 mg, preferably 0.2 to 50 mg of the ester derivative of 5-halogenated-2'-deoxyuridine respectively.

The ester derivative of 5-halogenated-2'-deoxyuridine of this invention can be administered in combination of appropriately selected two or more of its kinds.

The present invention is further described in detail by the following referential examples and examples.

REFERENTIAL EXAMPLE 1

Synthesis of 3',5'-dioctanoyl-5-fluoro-2'-deoxyuridine

A solution was obtained by dissolving 250 mg (1.01 m mole) of 5-fluoro-2'-deoxyuridine in 10 ml of pyridine anhydride and 590 mg (2.2 m mole) of octanoic acid anhydride and 1.2 mg (0.01 m mole) of dimethylaminopyridine were added thereto with stirring on the ice bath. The mixture was then stirred at room temperature overnight. The reaction mixture was poured into 50 ml of ice water and stirred for 30 minutes. Thereafter, 2N HCl was added to the reaction mixture to adjust its pH value to 4.0 and was then extracted three times with 20 ml of ethyl acetate. Ethyl acetate was removed by distillation at room temperature under reduced pressure and the obtained crude product was dissolved in dichloromethane and subjected to column chromatography on silica gel. The eluates from dichloromethane-ethanol (97:3)-(96:4) were collected and concentrated to obtain 3',5'-dioctanoyl-5-fluoro-2'-deoxyuridine.

The physical properties of this substance are as follows:

UV spectrum (ethanol) λ mas 213, 281 nm (2) $^1$H-NMR spectrum (chloroform-d) 6 value:
0.8–0.9 (6H, t—$CH_3$), 1.2–1.4 (20H, m, $\beta$-$CH_2$), 1.6–1.7 (4H, m, $\alpha$-$CH_2$), 2.4–2.6 (2H, m, $C_2'$), 4.3–4.5 (3H, m, $C_4'$, $C_5'$),
5.2–5.4 (1H, m, $C_3'$), 6.3 (1H, t, $C_1'$), 7.9 (1H, d, J=6.5Hz, $C_6$)

REFERENTIAL EXAMPLE 2

Synthesis of 3',5'-didecanoyl-5-fluoro-2'-deoxyuridine

A solution of 250 mg (1.01 m mole) of 5-fluoro-2'-deoxy uridine in 10 ml of pyridine anhydride was prepared and 720 mg (2.2 m mole) of decanoic acid anhydride and 1.2 mg (0.01 m mole) of dimethylaminopyridine were added to the solution with stirring on the ice bath. The mixture was then stirred at room temperature overnight. After the reaction mixture was poured into 50 ml of ice water and stirred for 30 minutes, the mixture had its pH adjusted to 4.0 with 2N HCl and was extracted three times with 20 ml of ethyl acetate. The crude product obtained after the removal of ethyl acetate by distillation at room temperature under reduced pressure was dissolved in dichloromethane and subjected to column chromatography on silica gel. The eluates from dichloromethane-ethanol (97:3)–(96:4) were pooled and concentrated to give 3',5'-didecanoyl-5-fluoro-2'-deoxyuridine.

The physical properties of this substance are as follows:

(1) UV spectrum (ethanol) λ max 213, 281 nm
(2) $^1$H-NMR spectrum (chloroform-d) δ value:
0.8–0.9 (6H, t, —CH$_3$), 1.2–1.4 (28H, m, β-CH$_2$), 1.6–1.7
(4H, m, α-CH$_2$), 2.4–2.6 (2H, m, C$_2$'), 4.3–4.5 (3H, m, C$_4$', C$_5$'), 5.2–5.4 (1H, m, C$_3$'), 6.3 (1H, t, C:'),'7.9 (1H, d, J=6.5Hz, C$_8$)

Synthesis of 3,5'-didodecanoyl-5-fluoro-2'-deoxyuridine

A solution was prepared by dissolving 250 mg (1.01 m mole) of 5-fluoro-2'-deoxyuridine in 10 ml of pyridine anhydride and 840 mg (2.2 m mole) of dodecanoic acid anhydride and 1.2 mg (0.01 m mole) of dimethylaminopyridine were added thereto with stirring on the ice bath. The admixture was further stirred overnight at room temperature. The reaction mixture was poured into 50 ml of ice water and stirred for 30 minutes. Thereafter the reaction mixture's pH was adjusted to 4.0 by adding 2N HCl and it was extracted three times with 20 ml of ethyl acetate. Ethyl acetate was then distilled away at room temperature under reduced pressure and the resulting crude product was dissolved in dichloromethane. The solution was subjected to column chromatography over silica gel and eluates from dichloromethane ethanol (98:2)-(97:3) were collected and concentrated to obtain 3',5'-didodecanoyl-5-fluoro-2'-deoxyuridine.

This substance has the following physical properties:
(1) UV spectrum (ethanol) λ max 213, 281 nm
($^1$H-NMR spectrum (chloroform-d) δ value:
0.8–0.9 (6H, t, —CH$_3$), 1.2–1.4
(36H, m, β-CH$_2$), 1.6–1.7 (4H, m, α-CH$_2$), 2.4–2.6 (2H, m, C$_2$'), 4.3–4.5 (3H, m, C$_4$', C$_5$'), 5.2–5.4 (1H, m, C$_3$'), 6,3 (1H, t, C$_1$'), 7.9 (1H, d, J=6.5 Hz, C$_6$)
(3) Melting point: 49°–50° C.

REFERENTIAL EXAMPLE 4

Synthesis of 3',5'-ditetradecanoyl-5-fluoro-2'-deoxyuridine

A solution of 250 mg (1.01 m mole) of 5-fluoro-2'-deoxyuridine in 10 ml of pyridine anhydride was prepared and then 960 mg (2.2 m mole) of tetradecanoic acid anhydride and 1.2 mg (0.01 m mole) of dimethylaminopyridine were added thereto with stirring while cooling with ice. The mixture was kept stirring over night at room temperature. After the reaction mixture was poured into 50 ml of ice water and stirred for 30 minutes, 2N HCl was added thereto to adjust its pH to 4.0 and the mixture was extracted three times with 20 ml of ethyl acetate. Ethyl acetate was removed by distillation at room temperature under reduced pressure and the obtained crude product was dissolved in dichloromethane. The solution was subjected to column chromatography over silica gel and the eluates obtained from dichloromethane-ethanol (98:2)–(97:3) were pooled and concentrated to give 3',5'-ditetradecanoyl-5-fluoro-2'-deoxyuridine.

This substance has the following physical properties:
(1) UV spectrum (ethanol) λ max 213, 281 nm
(2) $^1$H-NMR spectrum (chloroform-d) δ value:
0.8–0.9 (6H, t, —CH$_3$), 1.2–1.4 (44H, m, β-CH$_2$), 1.6–1.7 α-CH$_2$), 2.4–2.6 (2H, m, C$_2$'), 4.3–4.5 (3H, m, C$_4$', C$_5$'), 5.2–5.4 (1H, m, C$_3$'), 6.3 (1H, t, C$_1$'), 7.9 (1H, d, J=6.5 Hz, C$_6$)
(3) Melting point: 65–67° C.

REFERENTIAL EXAMPLE 5

Synthesis of 3',5'-dihexadecanoyl-5-fluoro-2'-deoxyuridine

A solution was prepared by dissolving 250 mg (1.01 m mole) of 5-fluoro-2'-deoxyuridine in 10 ml of pyridine anhydride, and 1100 mg (2.2 m mole) of hexadecanoic acid anhydride and 1.2 mg (0.01 m mole) of dimethylaminopyridine were added to the solution with stirring on the ice bath. The mixture was stirred overnight at room temperature. The reaction mixture was poured into 50 ml of ice water, stirred for 30 minutes, and its pH was adjusted to 4.0 by adding 2N HCl. Extraction was repeated three times with the use of 20 ml of ethyl acetate, and then ethyl acetate was distilled away at room temperature under reduced pressure. Thus obtained crude product was dissolved in dichloromethane and the solution was put to column chromatography on silica gel. The eluates from dichloromethane-ethanol (98:2)–(97:3) were collected and concentrated to obtain 3,5'-dihexadecanoyl-5-fluoro-2'-deoxyuridine.

This substance has physical properties as mentioned below:
(1) UV spectrum (ethanol) λ max 213, 281 nm
(2) $^1$H-NMR spectrum (chloroform-d) δ value 0.8–0.9 (6H, t, —CH$_3$), 1.2–1.4 (52H, m, 8-CH), 1.6-1.7 (4H, m, u-CH), 2.4–2.6 (2H, m, C'), 4.3–4.5 (3H, m, C', C'), 5.2–5.4 (1H, m, C'), 6.3 (1H, t, C'), 7.9 (1H, e, J=6.5 Hz, C$_8$)
Melting point: 74°–75° C.

REFERENTIAL EXAMPLE 6

Synthesis of 3',5'-dibenzoyl-5-fluoro-2'-deoxyuridine

A solution was prepared by dissolving 250 mg (1.01 m mole) of 5-fluoro-2'-deoxyuridine in 10 ml of pyridine anhydride, and 500 mg (2.2 m mole) of benzoic anhydride and 1.2 mg (0.01 m mole) of dimethylaminopyridine were added thereto with stirring while being cooled with ice. The mixture was stirred overnight at room temperature. The reaction mixture was poured into 50 ml of ice water and, after 30 minutes' stirring, pH of the mixture was adjusted to 4.0 with 2N HCl and was extracted three times with 20 ml of ethyl acetate. Methyl acetate was distilled away at room temperature under by diminished pressure and the resulting crude product was dissolved in dichloromethane to be subjected to column chromatography over silica gel. The eluates from dichloromethane-ethanol (98:2)–(97:3) were pooled and concentrated to obtain 3',5'-dibenzoyl-5-fluoro-2'deoxyuridine. The yield was 85%.

This substance has the following physical properties:
(1) UV spectrum (ethanol) λ max 267, 230 nm
(2) $^1$H-NMR spectrum (chloroform-d: methanol-d$_4$ (1:1)) δ value: 25–4.50 2.40–2.60 (2H, m, C$_2$), 4.25–4.50 (3H, m, C$_4$', C$_5$'), 5.1–5.40
(1H, m, C$_3$'), 6.25 (1H, t, Cl'), 7.30–7.60 (6H, m, benzoyl), 7.90 (1H, d, J=6.5 Hz, C$_6$) 8.00–8.15 (4H, m, benzoyl-β-CH)
(3) Melting point: 273°–274° C.

REFERENTIAL EXAMPLE 7

Synthesis of 3',5'-dioctanoyl-5-iodo-2'-deoxyuridine

A solution was prepared by dissolving 350 mg (0.99 m mole) of 5-iodo-2'-deoxyuridine in 5 ml of pyridine anhydride, and 600 mg (2.22 m mole) of octanoic anhydride and 1.2 mg (0.01 m mole) of dimethylaminopyridine were added to the solution with stirring on the ice bath. The mixture was kept stirring overnight at room temperature. The reaction mixture was poured into 50 ml of ice water, stirred for 30 minutes, and then had its pH value adjusted to 4.0 with 2N NCl. Thereafter, the mixture was extracted three times with 20 ml of chloroform. Chloroform was removed by distillation at room temperature under reduced pressure and the obtained crude product was dissolved in dichloromethane and subjected to column chromatography on silica gel. The eluates obtained from dichloroethane-ethanol (99:1)–(98:2) were pooled and concentrated to obtain 3',5') dioctanoyl-5-iodo-2'-deoxyuridine. The yield was 90%.

The physical properties of this substance are as follows:

(1) UV spectrum (ethanol) λ max 281, 213 nm $^1$H-NMR spectrum chloroform-d) δ value:
0.80 (6H, t, —CH$_3$), 1.05–1.70 (24H, m, —CH$_2$—), 2.10–2.70 (6H, m, C$_2$', —CO—CH$_2$—), 4.05–4.30 (3H, m, C$_4$', C$_5$'), 5.10–5.20 (1H, m, C$_3$'), 6.20 (1H, t, Cl'), 7.85 (1H, s, C$_6$)

EXAMPLE 1

Vero cells were cultured in Eagle minimum essential medium (MEM) containing 5% calf serum (CS) and were made to proliferate by means of monolayer cell culture. The cells were inoculated with 0.1 ml of herpes simplex type I virus (KOS strain) adjusted to 1,000 pfu/ml, which were allowed to hold on the host cells by adsorption for 1 hour at 37° C. Thereafter, the test compound, inclusive of the compounds of this invention, were added thereto respectively in concentration of 0.01~1,000 μg/ml.

After 48-hour culture in CS-MEM medium was over, the effective dose of each test compound which suppressed the formation of plaques by 50% in number (ED$_{50}$) and the minimum toxic dose (MTD) which caused the cytotoxicity were measured.

The result is shown in Table 1.

TABLE 1

| Test compound | ED$_{50}$ | MTD | Therapeutic index MTD/ED$_{50}$ |
|---|---|---|---|
| 9-(2-hydroxyethoxymethyl)guanine (Acyclovir) (Control compound) | 0.991 μg/ml | 1,000 μg/ml | 1,000 |
| 5-fluoro-2'-deoxyuridine (Control compound) | 0.01 μg/ml | 0.1 μg/ml | 10 |
| 3',5'-didodecanoyl-5-fluoro-2'-deoxyuridine (Compound of this invention) | 0.054 μg/ml | 100 μg/ml | 1,900 |
| 3',5'-ditetradecanoyl-5-fluoro-2'-deoxyuridine (Compound of this invention) | 0.049 μg/ml | 100 μg/ml | 2,000 |
| 3',5'-dihexadecanoyl-5-fluoro-2'-deoxyuridine (Compound of this invention) | 0.077 μg/ml | 150 μg/ml | 2,000 |

EXAMPLE 2

Vero cells were cultured in Eagle minimum 1 medium (MEM) containing 5% calf serum (CS) and were made to proliferate after the monolayer cell culture method. The cultured cells were inoculated with 0.1 ml of herpes simplex type I virus (KOS strain) of 10,000 pfu/ml concentration, which were left to be adsorbed by the host cells at 37° C. for 1 hour. The test compounds, inclusive of the compounds of this invention, were added to the cultures respectively in concentration of 0.001~1,000 μg/ml.

After 48-hour culture in 2% CS-MEM medium was over, the effective dose of each test compound which suppressed the formation of plaques by 50% in number (EDs) and the minimum toxic dose (MTD) which caused the cytotoxicity were measured.

The result is shown in Table 2.

TABLE 2

| Test compound | ED$_{50}$ | MTD | Therapeutic index MTD/ED$_{50}$ |
|---|---|---|---|
| 9-(2-hydroxyethoxymethyl)guanine (acyclovir) (Control compound) | 7.259 μg/ml | 1,000 μg/ml | 140 |
| 3',5'-dioctanoyl-5-fluoro-2'-deoxyuridine (Compound of this invention) | 0.018 μg/ml | 100 μg/ml | 5,600 |
| 3',5'-didecanoyl-5-fluoro-2'deoxyuridine (Compound of this invention) | 0.038 μg/ml | 100 μg/ml | 2,600 |

EXAMPLE 3

Vero cells. were cultured in Eagle essential medium (MEM) containing 5% fetal calf serum (FCS) and were made to proliferate after the monolayer cell culture method. The cells were inoculated with 0.1 ml of herpes simplex type I virus (KOS strain) of 2,000 pfu/ml concentration, which were made to be adsorbed by the host cells at 37° C. for 1 hour. The virus that were not yet adsorbed were washed away with a 2% CS-MEM medium and then test compounds, inclusive of the compounds of this invention, were added to the cultures respectively in concentration of 0.01~1,000 μg/ml.

After 48-hour culture in 2% CS-MEM medium was over, the effective dose of each test compound which suppressed the formation of plaques by 50% in number (ED$_{50}$) and the minimum toxic dose (MTD) which caused the cytotoxicity were measured.

The result is shown in Table 3.

TABLE 3

| Test compound | $ED_{50}$ | MTD | Therapeutic index $MTD/ED_{50}$ |
|---|---|---|---|
| 9-(2-hydroxyethoxymethyl)guanine (Acyclovir) (Control compound) | 3.363 μg/ml | 1,000 μg/ml | 279 |
| 3',5'-dibenzoyl-5-fluoro-2'-deoxyuridine (Compound of this invention) | 0.112 μg/ml | 100 μg/ml | 893 |
| 3',5'-dioctanoyl-5-iodo-2'-deoxyuridine (Control compound) | 0.285 μg/ml | 10 μg/ml | 35 |

As seen from Table 1, Table 2, and Table 3, the compound of this invention suppresses the proliferation of herpes simplex virus type I even at remarkably low concentration and also shows a very high therapeutic index which is expressed by a ratio of the toxicity against normal cells to the antiviral activity as compared with Acyclovia and 5-fluoro-2'-deoxyuridine that is 5-halogenated-2'deoxyuridine not induced to an ester derivative, which are now clinically used as the antiviral drug.

EXAMPLE 4

Manufacture of capsules

The following ingredients were mixed to prepare powder and capsules filled with thus prepared powder were manufactured according to the ordinary method.

| | |
|---|---|
| Compound of this invention (3',5'-dihexadecanoyl-5-fluoro-2'-deoxyuridine) | 10 mg |
| Lactose | 97 mg |
| Crystalline cellulose | 50 mg |
| Magnesium stearate | 3 mg |
| Total | 160 mg |

EXAMPLE 5

Manufacture of injections

A compound (3',5'-ditetradecanoyl-5-fluoro-2'-deoxyuridine) of this invention was dissolved in distilled water for injection (pH 6.00~7.50) to obtain an injection containing 0.3~1 mg of the compound per ml.

EXAMPLE 6

Manufacture of ointments

The following ingredients were thoroughly mixed and made into an ointment according to the ordinarily practiced method.

| | |
|---|---|
| Compound of this invention (3',5'-dioctanoyl-5-fluoro-2'-deoxyuridine) | 0.1 g |
| Diisopropyl adipate | 2.0 g |
| White soft paraffine | 7.9 g |
| Total | 10 g |

EXAMPLE 7

Manufacture of suppositories

The following ingredients were mixed well and formed into suppositories according to the ordinary method.

| | |
|---|---|
| Compound of this invention (3',5'-didecanoyl-5-fluoro-2'-deoxyuridine) | 5 mg |
| Witepsol (manufactured by Dynamit Nobel) (consisting of $C_{12}$–$C_{18}$ mono-, di-, and tri-glycerides) | 1,995 mg |
| Total | 2,000 mg |

EXAMPLE 8

Manufacture of eye ointments

The following ingredients were mixed to prepare an eye ointment according to the ordinary method.

| | |
|---|---|
| Compound of this invention (3',5'-didodecanoyl-5-fluoro-2'-deoxyuridine) | 0.1 g |
| Vaseline | 7.0 g |
| Liquid paraffin | 2.9 g |
| Total | 10 g |

Industrial Applications

An antiviral agent which contains a 5-halogenated-2'-deoxyuridine derivative of the present invention as the active ingredient displays a high level of antiviral effect with small doses and yet its toxicity to normal cells is low and accordingly can be used for the therapy of various kinds of viral infections.

We claim:

1. A method of inhibiting herpes simplex type I viral replication in a cell comprising administering an effective amount to inhibit herpes simplex type I viral replication in a cell of an esterified derivative of a 5-halogenated-2,'-deoxy-uridine expressed by the following formula

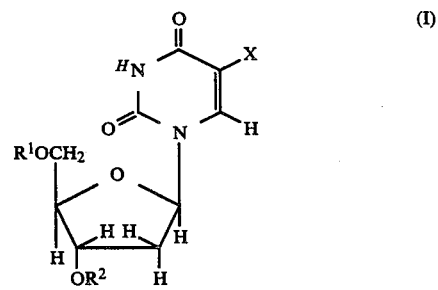

wherein X represents any one of F, Cl, and Br; $R^1$ and $R_2$ may be identical or different from each other, each representing a straight chain saturated aliphatic acyl group comprising eight to sixteen carbon atoms.

2. The method of claim 1, wherein X in formula (I) is a fluorine atom.

* * * * *